United States Patent [19]
Gall et al.

[11] Patent Number: 6,030,968
[45] Date of Patent: Feb. 29, 2000

[54] POSITIVE AMPA RECEPTOR MODULATION TO ENHANCE BRAIN NEUROTROPHIC FACTOR EXPRESSION

[75] Inventors: Christine M. Gall; Gary S. Lynch, both of Irvine; Julie C. Lauterborn, Huntington Beach; Peter W. Vanderklish, Laguna Beach, all of Calif.

[73] Assignee: The Regents of the University of California, Oakland, Calif.

[21] Appl. No.: 08/932,746

[22] Filed: Sep. 17, 1997

Related U.S. Application Data

[60] Provisional application No. 60/026,571, Sep. 17, 1996.
[51] Int. Cl.[7] .......................... A61K 31/54; A61K 31/535
[52] U.S. Cl. ....................................... 514/223.2; 514/230.2
[58] Field of Search ............................... 514/223.2, 230.2

[56] References Cited

U.S. PATENT DOCUMENTS

| | | | |
|---|---|---|---|
| 5,488,049 | 1/1996 | Costa et al. | 514/223.2 |
| 5,650,409 | 7/1997 | Rogers et al. | 514/230.2 |

FOREIGN PATENT DOCUMENTS

| | | | |
|---|---|---|---|
| 94/02475 | 2/1994 | WIPO | C07D 317/68 |
| 96/38414 | 12/1996 | WIPO | C07D 211/16 |

OTHER PUBLICATIONS

Cosi, Christina et al., "Glucocorticoids depress activity-dependent expression of BDNF mRNA in hippocampal neurones," *Neuro Report* (1993) vol. 4:527–530.

Eide, Fernette F., et al., "Neurotrophins and Their Receptors—Current Concepts and Implications for Neurologic Disease," *Experimental Neurology* (1993) vol. 121:200–214.

Kokaia, Zaal et al., "BDNF makes cultured dentate granule cells more resistant to hypoglycaemic damage," *Neuro Report* (1994) vol. 5:1241–1244.

Lauterborn, J. et al., "Cell–Specific Modulation of Basal and Seizure–Induced Neurotrophin Expression by Adrenalectomy," (1995) vol. 68, No. (2):363–378.

Lindsay, Ronald M., et al., "The Therapeutic Potential of Neurotrophic Factors in the Treatment of Parkinson's Disease," *Experimental Neurology* (1994) vol. 124:103–118.

Barinaga, Marcia, "Neurotrophic factors Enter the Clinic," *Science* (May 6, 1994) vol. 264:772–774.

Mattson, Mark P., et al., "Mechanisms of Neurotrophic Factor Protection against Calcium— and Free Radical–mediated Excitotoxic Injury: Implications for Treating Neurodegenerative Disorders," *Experimental Neurology* (1993) vol. 124:89–95.

Saporito, Michael S., et al., "Pharmacological Induction of Nerve Growth Factor mRNA in Adult Rat Brain," *Experimental Neurology* (1993) vol. 123:295–302.

Smith, Mark A., et al., "Stress and Glucocorticoids Affect the Expression of Brain–Derived Neurotrophic Factor and Neurotrophin–3 mRNAs in the Hippocampus," *The Journal of Neuroscience* (Mar. 1995) vol. 15, No. (3):1768–1777.

Yuen, Eric C., et al., "Neurotrophins and the Neurotrophic Factor Hypothesis," *Neural Notes* (1996) vol. 1, No. (4):3–7.

*Primary Examiner*—Kevine E. Weddington
*Attorney, Agent, or Firm*—Bozicevic, Field & Francis; Bret Field

[57] ABSTRACT

Methods for increasing the level of neurotrophic factors and neurotrophic factor receptors in the brain of a mammal afflicted with a pathology which produces neurodegeneration without significant loss of memory or learning comprising administering to a mammal an effective amount of an allosteric upmodulator of α-amino-3-hydroxy-5-methylisoxazole-4-proprionic acid (AMPA) receptors.

13 Claims, 5 Drawing Sheets

16  17 aniracetam  18  19

28
bendroflumethiazide

29
benzthiazide

30
buthiazide

31
chlorothiazide

32
cyclothiazide 33
epithiazide 34
hydrochlorothiazide 35
hydroflumethiazide

FIG. 1E

36
methylclothiazide

37
methalthiazide

38
polythiazide

39
trichlormethiazide

40

41

42

POSITIVE AMPA RECEPTOR MODULATION TO ENHANCE BRAIN NEUROTROPHIC FACTOR EXPRESSION

CROSS-REFERENCE TO RELATED APPLICATIONS

This application is a continuation in part of application Ser. No. 60/026,571, filed Sep. 17, 1996, the disclosure of which is herein incorporated by reference.

ACKNOWLEDGMENT

This invention was made with United States Government support under Grant No. NS26748 awarded by the National Institute of Neurological Disorders and stroke, Grant Nos. MHOO974 and MHOO358, awarded by the National Institutes of Mental Health, and Grant No. AGO0538, awarded by the National Institute of Aging. The United States Government has certain rights in this invention.

INTRODUCTION

1. Field of the Invention

The field of the invention is the modulation of mammalian neurotrophic factor expression.

2. Background of the Invention

Neurotrophic factors include a number of families of endogenous substances that support the survival and, in some instances, the growth and biosynthetic activities of neurons. A tremendous interest in neurotrophic factors has developed in the hope that they might be used to protect against the neurodegenerative effects of disease (e.g., Parkinson's disease. amyotrophic lateral sclerosis, Alzheirner's disease), normal aging, and physical trauma to the brain. See, e.g., Barinaga. M., et al., Science (Editorial commentary) 264: 772–774 (1994); Eide, F. F., et al., Exp. Neurol.121: 200–214 (1993), and Experimental Neurology (vol. 124, #1, (1993).

The therapeutic use of neurotrophic factors has centered around (i) infusion of erogenous factors into the brain (Fischer, W., et al., Nature 1987: 65–68 (1991)), (ii) implantation of cells genetically engineered cells to secrete factors into the brain (Gage, F. H., et al., Trends. Neurosci. 14: 328–333 (1991); Stromberg, C. J. et: al., J. Neurosci. Res. 25: 405–411 (1990)), and (iii) the design of techniques for the transport of peripherally applied trophic activities across the blood brain barrier and into the brain (normally the blood brain barrier prevents penetration). There have been fewer efforts designed to identify peripheral agents that can increase endogenous expression in the brain (Carswell, S. Exp. Neurol. 123: 36–423 (1993); Saporito, M. S., et al., Exp. Neurol. 123: 295–302 (1993)). A significant disadvantage of these methods is the requirement for invasive procedures or the use of direct neurotransmitter agonists which readily induce seizures and/or disrupt normal neuronal function.

In the last few years there have been reports that neuronal activity leads to an increase in the expression of several neurotrophic factors produced by peripheral and brain neurons. For most factors evidence is limited to the demonstration that extreme levels of activity (e.g., seizures) stimulate increases in transcription. For the neurotrophins, increases in mRNA content have been demonstrated with subseizure electrical stimulation (Castrén, E., et al., NeuroReport 4: 895–898 (1993); Dragunow. M., et al., Neurosci. Lett. 160: 232–236 (1993); Patterson, S. L., et al., Neuron 9:1081–1088 (1992)), in visual cortex following exposure of a dark reared animal to light (Castrén, E., et al., Proc. Natl. Acad. Sci., USA 89: 9444–9448 (1992)), and in animals exposed to a complex training environment (Falkenberg, T., et al., Neurosci. Lett. 138: 153–156 (1992)).

Moreover, the results of studies of cultured neurons, and fewer studies of drug effects in vivo, indicate that increases in neurotrophin expression by telencephalic neurons can be affected by general depolarizing agents (e.g., treatment with KCl) (Ghosh. A., et al., Science 263: 1618–1623 (1994)) and by depolarization through glutamate receptor activation (i.e., treatment with kainic acid, glutamate. NMDA) (Bessho. Y., S., et al., Mol. Brain Res. 18: 201–208 (1993); Ghosh. A., et: al., Science 263: 1618–1623 (1994); Gwag, B., et al., Exp. Neurol. 121: 160–171 (1993); Rivera, S., Soc. Neurosci. Abstr. 19:258 (1993); Zaf ra, F., et al., Neurosci.12: 4793–4799(1992)). Thus, methods of increasing neuronal activity involved imposing or removing conditions far removed from naturally occurring events to disrupt normal brain functions.

U.S. Pat. No. 5,488,049 of Costa et al. is directed to the treatment of learning and memory disorders using benzothiadiazide derivatives as nootropic agents. Within the meaning of memory or learning disorders as disclosed in Costa et al. are memory and learning disorders resulting from trauma, stroke, epilepsy, and neurodegenerative disorders; and learning and memory disorders associated with senile dementia such as Alzheimer's disease, alcohol intoxication, and neurotoxic agents such as PCP. However, Costa et al. does not disclose the treatment of neurological pathologies not affecting learning and memory such as motor neuron degeneration, perceptual disorders, logic impairments, attention impairments, and deficits in the comprehension and use of language.

What is needed in the art is a non-invasive means to induce the increased expression of neurotrophic factors or neurotrophic factor receptors. In particular, what is needed is a means to induce expression of neurotrophic receptors or neurotrophic factors in a mammal afflicted with a neurodegenerative pathology not significantly affecting memory and learning where induction is accomplished using compounds which: cross the blood-brain barrier, are effective at doses that have no known toxic consequences, have been tested for safety in humans, and do not directly depolarize brain neurons. Quite surprisingly, the present invention provides these and other advantages.

SUMMARY OF THE INVENTION

In one aspect, the present invention is directed to a method for increasing the level of neurotrophic factors in a mammalian brain in a mammal in need of an increased neurotrophic factor. The method includes administering an amount of allosteric upmodulator of α-amino-3-hydroxy-5-methyl-isoxazole-4-proprionic acid ("AMPA") receptors to the mammal in an amount etfective to increase the expression of neurotrophic factors and where the mammal is afflicted with a pathology which produces neurodegeneration without significant loss of memory or learning.

In one embodiment, the pathology is selected from the group comprising: Parkinson's Disease, amyotrophic lateral sclerosis (ALS), stroke, direct trauma, Huntington's disease, epilepsy, Down's Syndrome, hypoglycemia, and hypoxia. Generally, the mammalian brain is a human brain.

In another embodiment, the neurotrophic factors are selected from at least one of the following factors: brain derived neurotrophic factor, fibroblast growth factors, neurotrophin 3, nerve growth factor, neurotrophin 4/5, glial cell line derived neurotrophic factor, ciliary neurotrophic factor, leukemia inhibitory factor, transforming growth factors, and platelet-derived growth factor.

In another aspect, the present invention is directed to an in vitro method of inducing neurotrophic factors in mammalian brain tissue. The method comprises the steps of contacting the tissue with an amount of an allosteric upmodulator of the AMPA receptor which is effective in increasing the expression of neurotrophic factors, and detecting the expression of neurotrophic factors.

In one embodiment, the brain tissue is from the hippocampus. In another embodiment, the detecting step includes hybridization of a nucleic acid complementary to mRNA encoding the factors. In yet another embodiment, the detecting step includes in situ hybridization of nucleic acid complementary to mRNA encoding the factors.

In an additional aspect, the present invention is directed to a method for increasing the level of neurotrophic factor receptors in a mammalian brain in a mammal in need of increased neurotrophic factor receptors by administering an amount of allosteric upmodulator of α-amino-3-hydroxy-5-methyl-isoxazole-4-proprionic acid ("AMPA") receptors, where the amount is effective in increasing the expression of the neurotrophic factor receptors and where the mammal is afflicted with a pathology which produces neurodegeneration without significant loss of memory or learning. In one embodiment the allosteric modulator is LiD37 (listed herein as compound 27) or DP75. In another embodiment the allosteric upmodulators are blood-brain barrier permeant. In yet another embodiment, the neurotrophic receptor is the TrkB receptor. Alternative embodiments of the foregoing aspects of the present invention may be had by reference to the disclosure as a whole.

DETAILED DESCRIPTION OF THE INVENTION

The present invention is directed to the use of allosteric upmodulators of AMPA receptors to increase the levels of neurotrophic factors in mammalian brains. The present invention is also directed to the use of allosteric upmodulators to increase the levels of neurotrophic factor receptors. The methods of the present invention are useful in in vitro applications as, for example, a means to increase the amount of neurotrophic factor or neurotrophic factor receptors so as to aid in the identification of these cell types in a cultured neuropathological sample.

The invention is also useful in the treatment of disorders leading to neuronal degeneration without significant loss of memory or learning. This includes neurodegenerative conditions of sensory neural systems, of motor neural systems, of homeostatic/visceral control neural systems (i.e., hypothalamic and brainstem nuclei) as well as of cortical regions which, when damaged, give rise to impairments of higher mental functions other than learning and memory (e.g., stroke within Broca's area in the inferior frontal gyrus would cause deficiencies in the ability to speak without detectable learning and memory impairment; stoke in parts of parietal cortex would cause problems in attention to components of personal and/or visual space, in a syndrome called "visual neglect", without notable cognitive dysfunction).

The methods of the present invention involve the administration of allosteric upmodulators of α-amino-3-hydroxy-5-methyl-isoxazole-4-proprionic acid receptor which act, not by directly stimulating neural activity, but by upmodulating neural activation and transmission in neurons that contain glutamatergic receptors. These compounds bind to the glutamate receptor and. upon binding of a receptor agonist, allow an ion flux through the receptor of increased duration.

Subclasses of glutamate receptors mediate excitatory amino acid neurotransmitter effects. Glutamate, amongst the most abundant of all neurotransmitters, functions to promote rapid neurotransmitter-induced depolarization by opening membrane channels that permit the movement of sodium and potassium ions. These rapid effects are mediated by three receptor subtypes, each of which is identified by specific ligand binding with kainate, AMPA, and N-methyl-D-aspartate (NMDA).

Definitions

Units, prefixes, and symbols may be denoted in their SI accepted form. For purposes of the present invention, the following terms are defined below.

As used herein "neurotrophic factors" means polypeptides that support the growth, differentiation, and survival of neurons in the developing nervous system and maintain neurons and their biosynthetic activities in the mature nervous system. Exemplary neurotrophic factors include, but are not limited to, neurotrophins (e.g., nerve growth factor (NGF), brain-derived neurotrophic factor (BDNF), neurotrophin-3 (NT-3), neurotrophin-4/5 (NT-4/5)), neuropoietins (e.g., ciliary neurotrophic factor (CNTF), leukemia inhibitory factor (LIF)), insulin-like growth factors (e.g. insulin-like growth factor-1 (IGF-1), insulin-like growth factor-II (IGF-II)), transforming growth factor beta (e.g., transforming growth factor β(TGFβ$_1$, TGFβ$_2$, TGFβ$_3$)) fibroblast growth factors (e.g. acidic fibroblast growth factor (aFGF), basic fibroblast growth factor (bFGF), fibroblast growth factor-5 (FGF-5)), and others such as transforming growth factor alpha (TGF-α), platelet-derived growth factor (PDGF: AA, AB, and BB isoforms), and stem cell factor.

As used herein, "mammal" or "mammalian" means or relates to the class mammalia including the orders carnivore (e.g., dogs and cats). rodentia (e.g., mice. guinea pigs, and rats), and primates (e.g., humans, chimpanzees, and monkeys).

As used herein, "brain tissue" means individual or aggregates of cells from the brain. The cells may be obtained from cell culture of brain cells or directly from the brain or may be in the brain.

As used herein, "allosteric upmodulator" means a compound which acts upon and increases the activity of an enzyme or receptor. An allosteric upmodulator of an AMPA receptor increases ligand induced current flow through the receptor but has no effect until the receptor's ligand is bound.

As used herein, "α-amino-3-hydroxy-5-methyl-isoxazole-4-proprionic acid receptor" or "AMPA receptor" refers to the class of glutamatergic receptors which are present in cells, particularly neurons, usually at their surface membrane that recognize and bind to glutamate or AMPA. The binding of AMPA or glutamate to an AMPA receptor normally gives rise to a series of molecular events or reactions that result in a biological response. The biological response may be the activation or potentiation of a nervous impulse, changes in cellular secretion or metabolism, causing the cells to undergo differentiation or movement, or increasing the levels of nucleic acids coding for neurotrophic factors or neurotrophic factor receptors.

As used herein, "effective amount" or "amount effective to" or "therapeutically effective amount" means a dosage sufficient to produce a desired result. Generally, the desired result is an increase in neurotrophic factor expression or neurotrophic factor receptor expression.

As used herein, "a pathology which produces neurodegeneration" means a disease, metabolic disorder, direct physical or chemical insult, or any physiological process causing or participating in neuronal injury or death.

As used herein, "hypoxia" means a deficiency of oxygen reaching the tissues of the body.

As used herein, "cerebral stroke" means a rupture or obstruction (as by a clot) of an artery of the brain.

As used herein, "direct trauma" means an injury to the brain caused by physical contact without an intervening agency or step.

As used herein, "without significant loss of memory or learning" means a statistically insignificant decline in memory or learning assessed over time by the Randt Memory Test (Randt et al., Clin. Neuropsychol., 1980, 2: 184), Wechsler Memory Scale (J. Psych. 19:87–95 (1945), Forward Digit Span test (Craik, Age Differences in Human Memory, in: Handbook of the Psychology of Aging, Birren, J., and Schaie, K. (Eds.), New York, Van Nostrand (1977), Mini-Mental State Exam (Folstein et al., J. of Psych. Res. 12:189–192 (1975), or California Verbal Learning Test (CVLT) wherein such non-neurodegenerative pathological factors as aging, anxiety, fatigue, anger, depression, confusion, or vigor are controlled for. See, U.S. Pat. No. 5,063,206. Methods for assessing and controlling for subjective factors not caused by a pathology which causes neurodegeneration is known in the art and determined by such standard clinical tests such as the BECK Depression Scale, Spielberger Trait State Anxiety test, and POMS test (Profile of Mood State). The time interval between administration of one or more tests of memory or learning is of sufficient length to detect the presence of a statistically significant decline in memory or learning (should one exist) beyond that resulting from factors not related to a neurodegenerative pathology (e.g., age).

As used herein, "in need of increased neurotrophic factors" means a clinically assessed need to inhibit, suspend, or mitigate the progression or occurrence of a pathology which produces neurodegeneration or sublethal neuronal pathology without significant loss of memory and learning and to which end an increase in neurotropic factors or neurotrophic factor receptors in the brain is recommended by one of skill in the art of treating the particular pathology.

As used herein, "contact" or "contacting" means to place in direct physical association.

As used herein, "blood-brain barrier permeant" or "blood-brain barrier permeable" means that at equilibrium the ratio of a compound's distribution in the cerebro-spinal fluid (CSF) relative to its distribution in the plasma (CSF/plasma ratio) is greater than 0.01, generally at least 0.02, preferably at least 0.05, and most preferably at least 0.1.

As used herein, "neurotrophic factor receptor" means receptors which act as a target for neurotrophic factors including, but not limited to, the Trk family (e.g., TrkA, TrkB, and TrkC); the CNTF receptor complex (e.g., CNTFRα, gp130, LIFRβ); LIF receptor complex (e.g., gp130, LIFRP); IGF Type 1 receptor; insulin receptor; TGFβ type I, II, and III receptors; GFG receptors 1–4; epidermal growth factor receptor (EGFR); PDGF α- and β-receptors; c-kit.

"In vitro" means outside the body of the organism from which a cell or cells is obtained or from which a cell line is isolated. In contrast, by "in vivo" is meant within the body of the organism from which the cell was obtained or from which a cell line is isolated.

As used herein, "increasing the level" in reference to a particular compound, means to cause a detectable increase in the amount of the referenced compound.

As used herein, "increasing the expression" in reference to a particular protein means to cause a detectable increase in the amount of transcription product encoding the referenced protein. Typically, the transcription product assayed for is mRNA. An increase in transcription product may be caused by any number of means including increased transcription rate or decreased degradation rate.

Neurodegenerative Pathologies

The present invention provides for an increase in the levels of neurotrophic factors and their receptors in mammalian brains. Thus, the methods disclosed herein provide therapeutic benefit to mammals afflicted with, or diagnosed as having, a neurodegenerative pathology. In particular, the present invention is beneficial in the treatment of neurodegenerative pathologies including. but not limited to those, arising from a disease state and/or having an excitotoxic/ischemic mechanism.

Pathologies that would benefit from this invention include conditions (diseases and insults) leading to neuronal cell death and/or sub-lethal neuronal pathology including. for example: diseases of central motor systems including degenerative conditions affecting the basal ganglia (Huntington's disease, Wilson's disease, Striatonigral degeneration, corticobasal ganglionic degeneration), Tourettes syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration;

diseases affecting sensory neurons such as Friedreich's ataxia, diabetes, peripheral neuropathy, retinal neuronal degeneration;

diseases of limbic and cortical systems such as cerebral amyloidosis, Pick's atrophy, Retts syndrome;

neurodegenerative pathologies not causing significant loss of memory or learning involving multiple neuronal systems and/or brainstem including Leigh's disease, diffuse Lewy body disease, epilepsy, Multiple system atrophy, Guillain-Barre syndrome, lysosomal storage disorders such as lipofuscinosis, degenerative stages of Down's syndrome, Alper's disease, vertigo as result of CNS degeneration;

pathologies arising with aging and chronic alcohol or drug abuse including, for example, with alcoholism the degeneration of neurons in locus coeruleus and cerebellum; with aging degeneration of cerebellar neurons and cortical neurons leading to cognitive and motor impairments; and with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia or direct trauma;

pathologies arising as a negative side-effect of therapeutic drugs and treatments (e.g., degeneration of cingulate and entorhinal cortex neurons in response to anticonvulsant doses of antagonists of the NMDA class of glutamate receptor).

Mammals displaying clinical manifestations of a neurodegenerative pathology and in need of the therapeutic benefit derived from an increase in neurotrophic factors or neurotrophic factor receptors can be administered allosteric modulators according to the methods provided herein. Therapeutic benefit includes any of a number ot subjective or objective factors indicating a response of the condition being treated. This includes measures of increased neuronal survival or more normal function of surviving brain areas. For instance, some subjective symptoms of neurodegenerative disorders include pain. change in sensation including decreased sensation, muscle weakness, coordination problems, imbalance, neurasthenia, malaise, decreased reaction times, tremors, confusion, uncontrollable movement, lack of affect, obsessive/compulsive behavior, aphasia, agnosia, and visual neglect. Frequently objective signs, or signs observable by the physician or the health care provider, overlap with subjective signs. Examples include the physician's observation of signs such as decreased reaction time, muscle faciculations, tremors, rigidity, spasticity, muscle weakness, poor coordination, disorientation, dysphasia, dysarthria, and imbalance. Additionally, objective signs can include laboratory parameters such as the assessment of neural tissue loss and function by Positron Emission Tomography (PET) or functional Magnetic Resonance Imaging (MRI), blood tests, biopsies and electrical studies such as electromyographic data.

Also, macroscopic methods of evaluating the effects of the invention can be used which may be invasive or non-invasive. Further examples of evidence of a therapeutic benefit include clinical evaluations of cognitive functions including, object identification, increased performance speed of defined tasks as compared to pretreatment performance speeds, and nerve conduction velocity studies.

Evaluation of features such as speed of performing defined tasks, and nerve conduction studies could also be used to indicate that appropriate trk receptors have been activated. Any of the features relating to therapeutic benefits can be examples of improved neuronal function.

Allosteric-Ulpmodulators

A. Identifying by Function

Compounds useful in the practice of this invention are generally those which amplify (upmodulate) the activity of the natural stimulators of AMPA receptors, particularly by amplifying excitatory synaptic responses. Described herein are a wide variety of diverse compounds suitable tor use in the invention. See, International P3atent Application Publication No. WO 94/02475 (PCT/US93/06916). Methods for identifying other compounds are routine. They involve a variety of accepted tests to determine whether a given candidate compound is an upmodulator of the AMPA receptor. The primary assay is measurement of enlargement of the excitatory postsynaptic potential (EPSP) in in vitro brain slices, such as rat hippocampal brain slices.

In this assay, slices of hippocampus from a mammal such as rat are prepared and maintained in an interface chamber using conventional methods. Field EPSPs are recorded in the stratum radiatum of region CA1b and elicited by single stimulation pulses delivered once per 20 seconds to a bipolar electrode positioned in the Schaffer-commissural projections (see Granger, R et al., 1993, *Synapse*, 15:326–329; Staubli, U. et al., 1994a, *Proc. Natl. Acad. Sci.*, 91:777–781; and Staubli, U. et al., 1994b, *Proc. Natl. Acad. Sci.*, 91:11158–11162; Arai, A. et al., 1994, *Brain Res.*, 638:343–346; Arai, A. et al. 1996a, *Neuroscience* 75:573–585, and Arai et al., 1996b, J. Pharm. Exp. Ther. 278:627–638.

The wave form of a normal monosynaptic response is composed of:

an AMPA component, which has a relatively rapid rise time in the depolarizing direction (about 5–10 msec) and which decays within about 20 msec;

an NMDA component (slow rise time of about 30–40 msec and slow decay of about 40–70 msec)—the NMDA portion will not appear in normal CSF media, due to the voltage requirement for NMDA receptor channel activation, but in low magnesium media, an NMDA component may appear, and a GABA component in the opposite (hyperpolarizing) direction as the glutamatergic (AMPA and NMDA) components, exhibiting a time course with a rise time of about 10–20 msec and very slow decay (about 50–100 msec or more).

The different components can be separately measured to assay the effect of a putative AMPA receptor enhancing agent. This is accomplished by adding agents that block the unwanted components, so that the detectable responses are essentially only AMPA responses. For example, to measure AMPA responses. an NMDA receptor blocker (for example, AP-5 or other NMDA blockers known in the art) and/or a GABA blocker (for example, picrotoxin or other GABA blockers known in the art) are added to the slice. To prevent epileptiform activity in the GABA-blocked slices, known agents such as tetrodotoxin may be used.

AMPA up-modulators useful in the present invention are substances that cause an increased ion flux through the AMPA receptor complex channels in response to glutamatergic stimulation. Increased ion flux is typically measured as one or more of the following non-limiting parameters: at least a 10% increase in decay time, amplitude of the waveform and/or the area under the curve of the waveform and/or a decrease of at least 10% in rise time of the waveform, for example in preparations treated to block NMDA and GABA components. The increase or decrease is preferably at least 25–50%; most preferably it is at least 100%. How the increased ion flux is accomplished (for example, increased amplitude or increased decay time) is of secondary importance; up-modulation is reflective of increased ion fluxes through the AMPA channels, however achieved.

An additional and more detailed assay is that of excised patches, i.e., membrane patches excised from cultured hippocampal slices; methods are described in Arai et al., 1994. Outside-out patches are obtained from pyramidal hippocampal neurons and transferred to a recording chamber. Glutamate pulses are applied and data are collected with a patch clamp amplifier and digitized (Arai et al., 1994, 1996a,b). Because no GABA is applied to the patch, GABAergic currents will not be elicited. Any NMDA currents can be blocked as above (for example, with AP-5).

The central action of a compound can be verified by measurement of synaptic responses or the overall activity of brain cells in behaving animals (see Staubli et al., 1994a) and time course of biodistribution can be ascertained via injection and subsequent quantitation of drug levels in various tissue samples. Quantitation can be accomplished by methods known to those skilled in the art and will vary depending on the chemical nature of the drug.

B. Specific Compounds

Figure 1A:
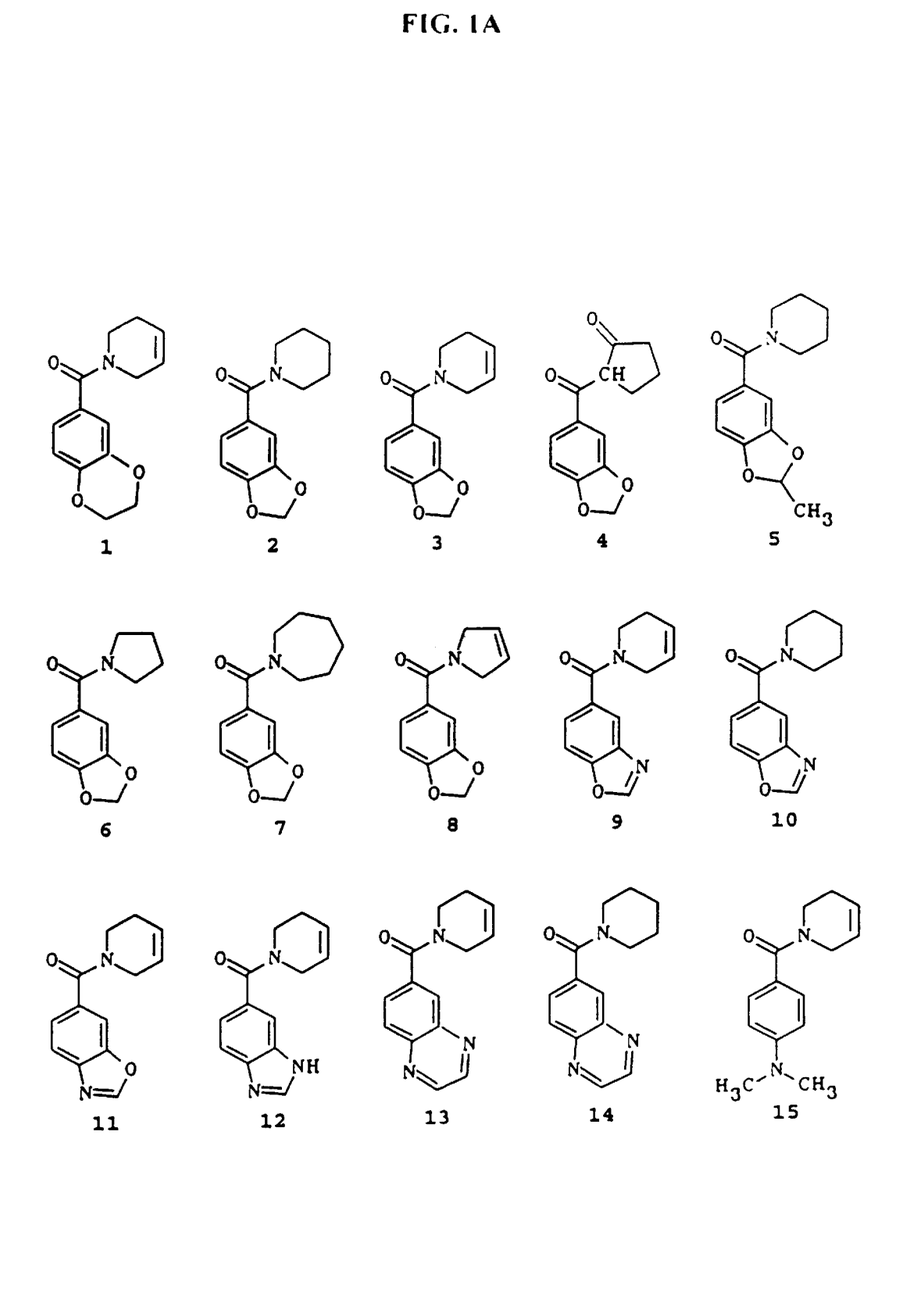
FIG. 1A–E provides the structures of a plurality of representative AMPA up-regulator compounds that find use in the subject invention.
Figure 1B:
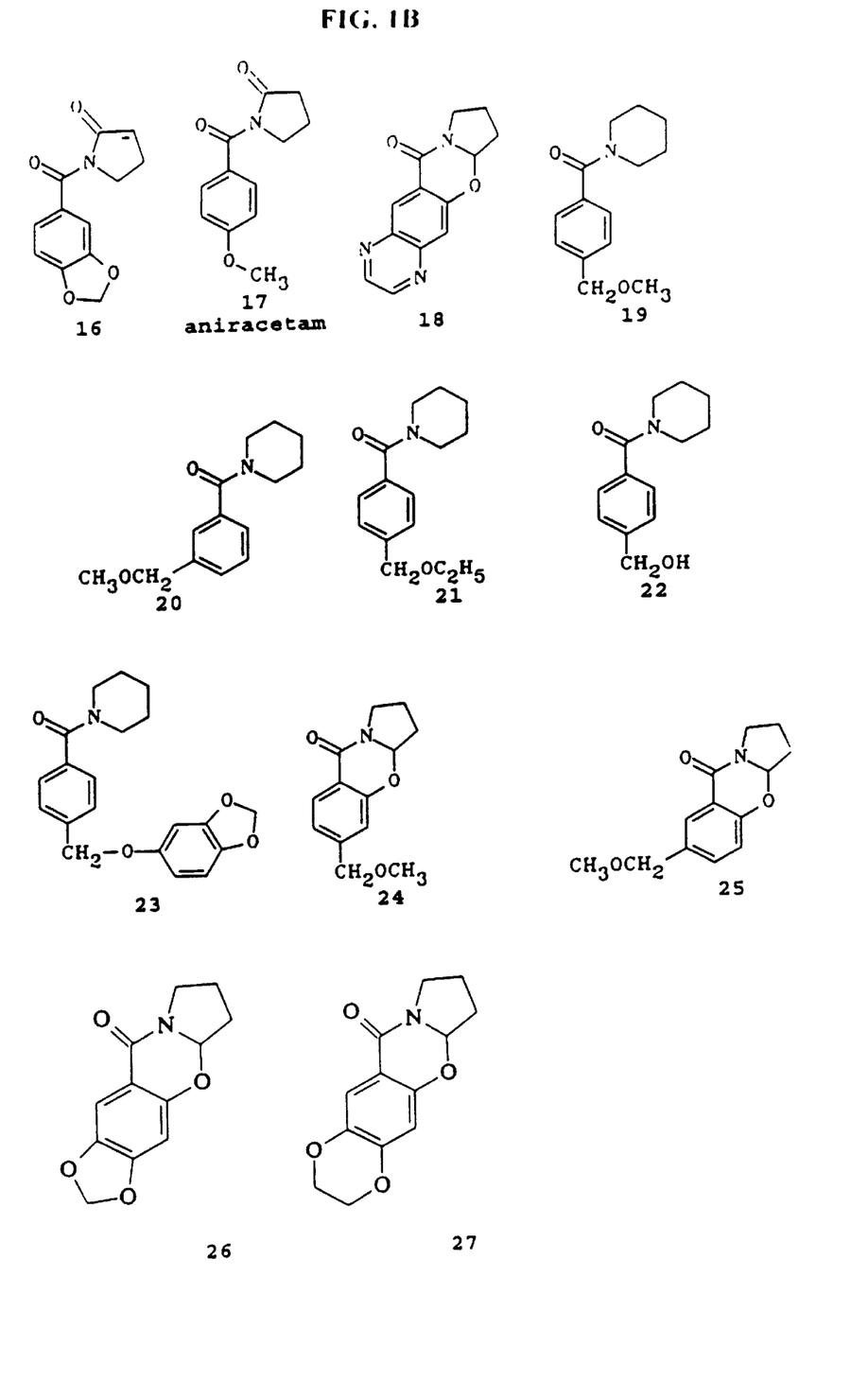
Figure 1C:
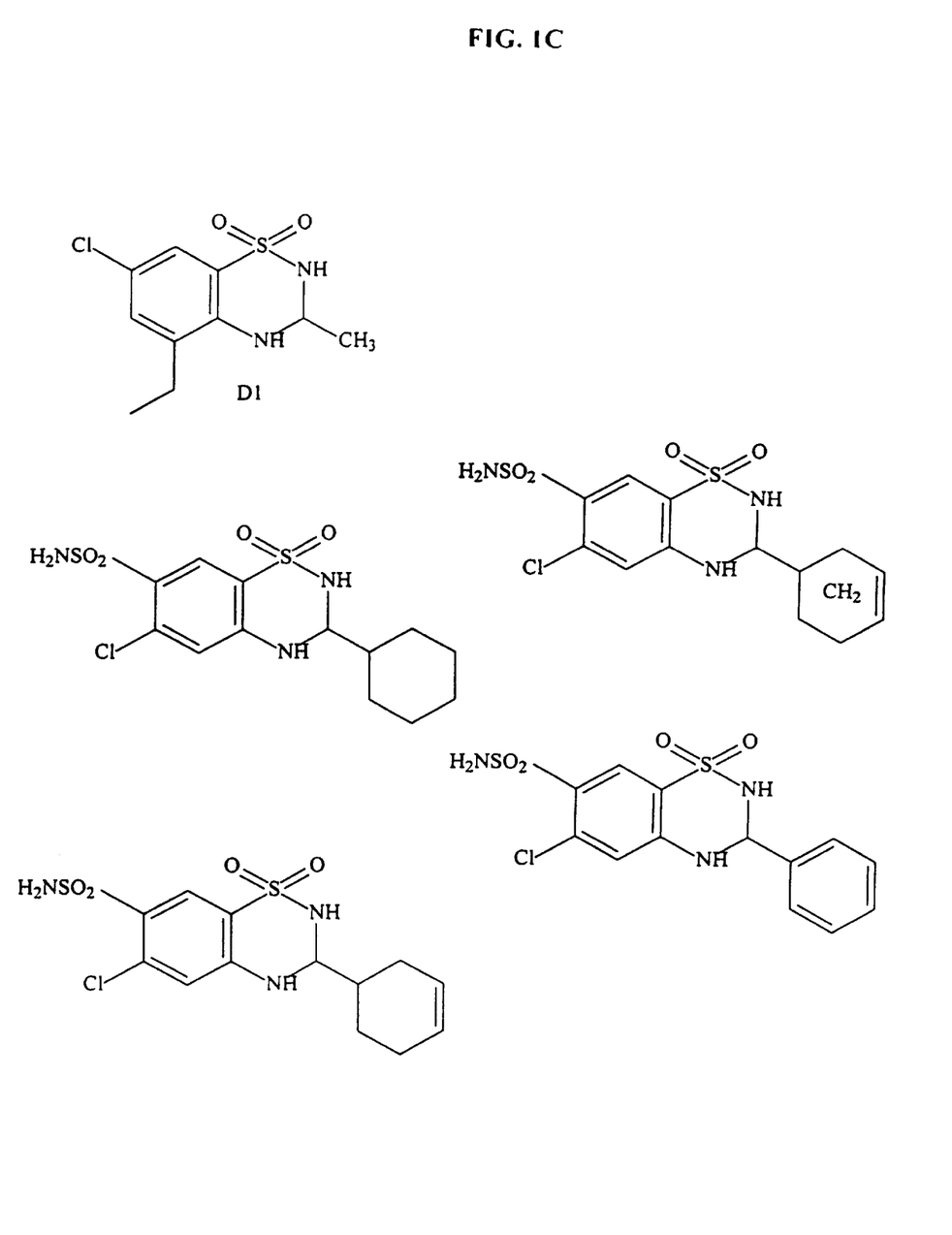
Figure 1D:
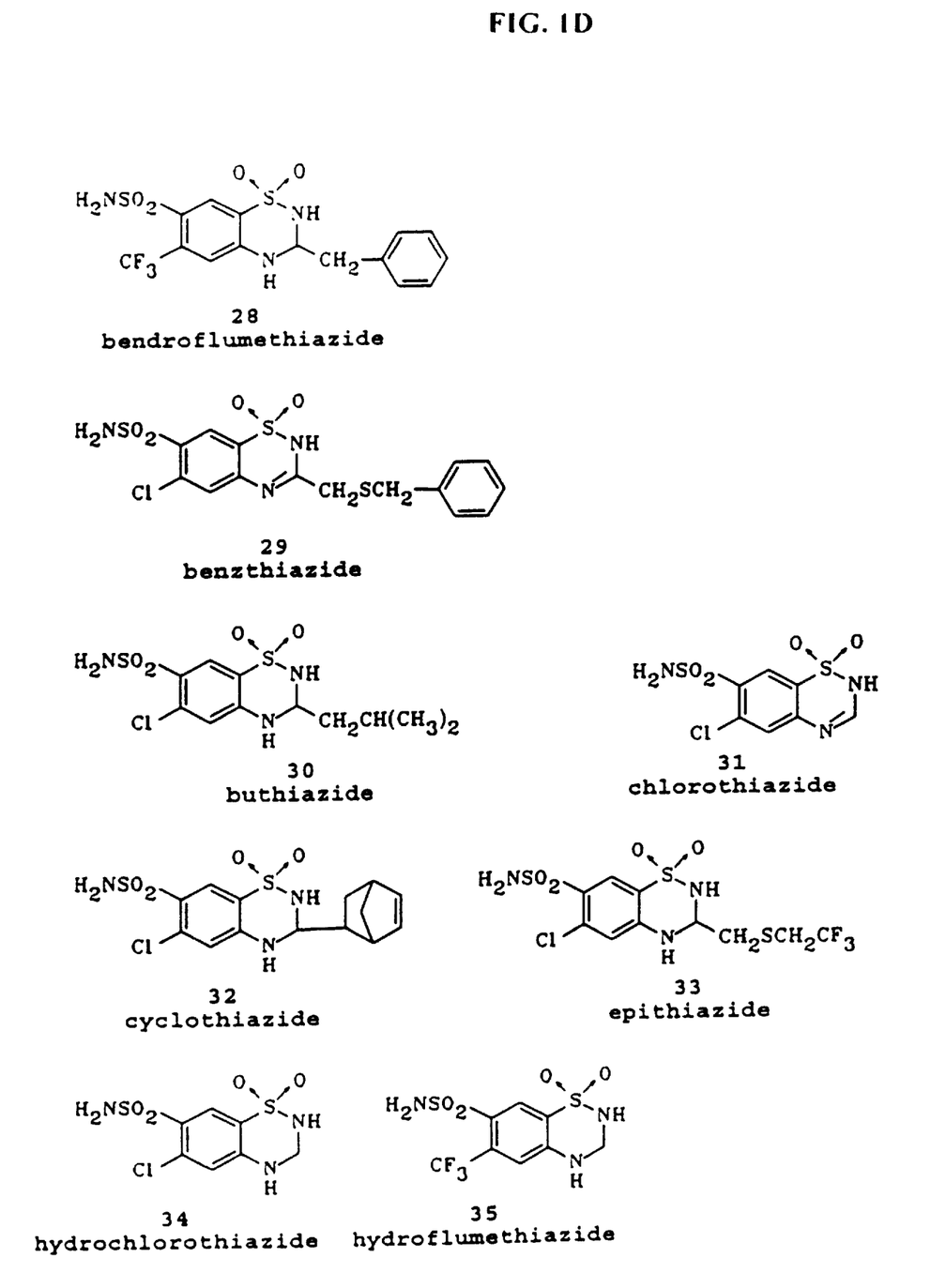
Figure 1E:
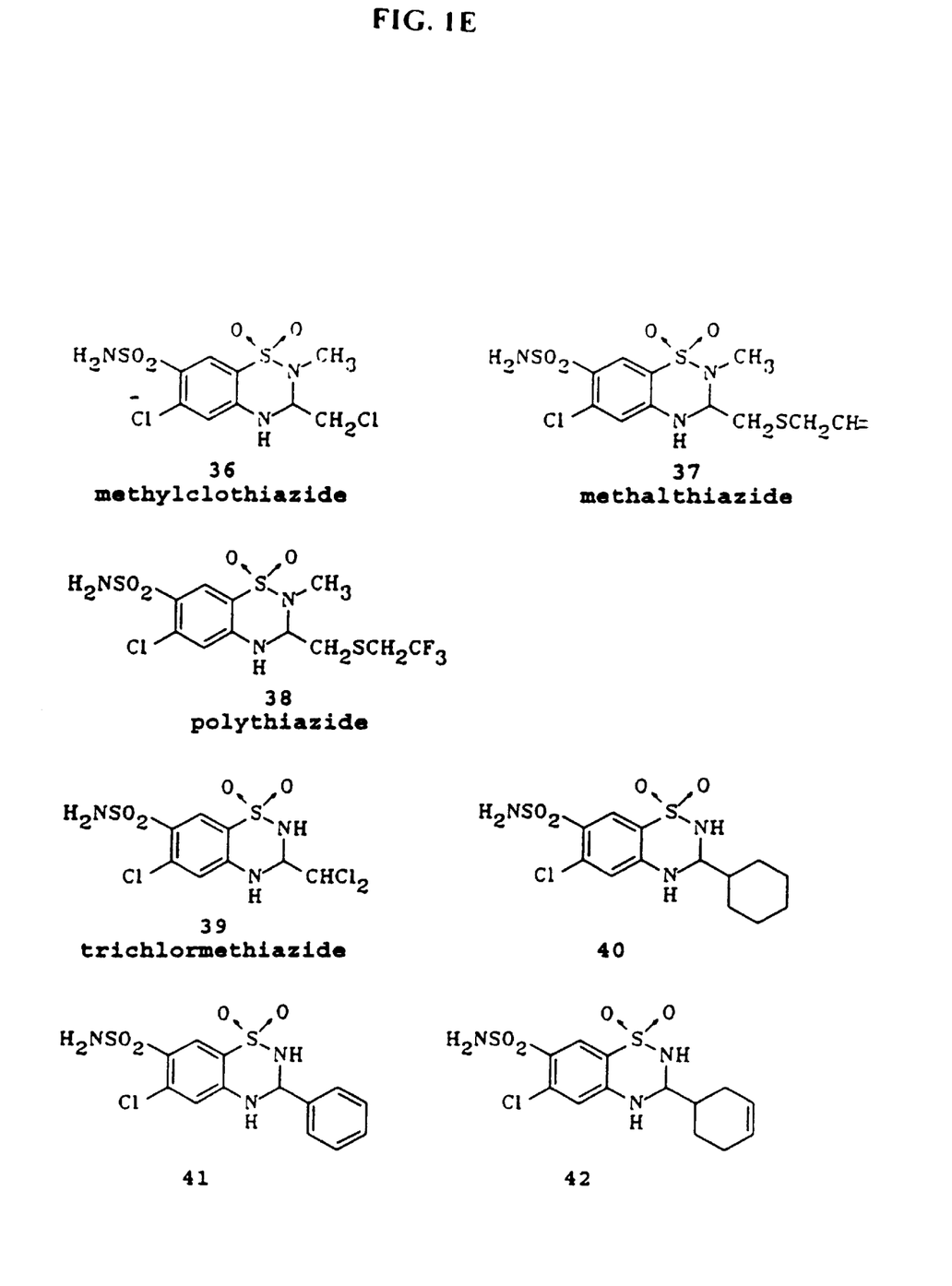

Compounds useful in the practice of this invention are generally those that amplify the activity of the natural stimulators of AMPA receptors. particularly bv amplifying excitatory synaptic response as defined above, i.e. AMPA upregulators. AMPA upregulators that find use in the subject invention include the "ampakines" described: in WO 94/02475 (PCT/US93/06916); U.S. Pat. No. 5,650,409; U.S. patent application Ser. No. 08/424,335; and U.S. patent application Ser. No. 08/853,221; as well as WO98/12185; the disclosures of which applications are expressly incorporated herein by reference. Particular compounds of interest include: aniracetam, 7-chloro-3-methyl-3-4-dihydro-2H-1, 2,4 benzothiadiazine S,S, dioxide, (see Zivkovic et al., 1995, J. Pharmacol. Exp. Therap., 272:300–309; Thompson et al., 1995, Proc. Nat. Acad. Sci. USA, 92:7667–7671) and those compounds shown in FIGS. 1A–1E.

Administration of Allosteric Upmodulators

The compounds, i.e., allosteric upmodulators, of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the compounds can be achieved in various ways, including oral, buccal, rectal, parenteral, intraperitoneal, intradermal, transdermal, inhaleal. etc., administration. Preferably, the allosteric upmodulators will be sufficiently blood-brain permeable so that their administration into the systemic circulation will result in a therapeutically effective amount in the brain.

The compounds of the present invention can be administered alone, in combination with each other, or they can be used in combination with other known compounds (e.g., other memory or learning enhancing agents). In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository. contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Preferred formulations of the compounds are oral preparations, particularly capsules or tablets containing each from about 10 milligrams up to about 1000 milligrams of active ingredient. The compounds are formulated in a variety of physiologically compatible matrixes or solvents suitable for ingestion or injection.

Preferred Dosages

The compounds, i.e., allosteric upmodulators, of the present invention are administered at a dosage that increases synaptic responses mediated by AMPA receptors while minimizing any side-effects. It is contemplated that the composition will be obtained and used under the guidance of a physician.

Typical dosages for systemic administration range from 0.1 to 50 milligrams per kg weight of subject per administration. A typical dosage may be one 10–500 mg tablet taken once a day, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds that stimulate glutamatergic receptors are more potent than others. Preferred dosages for a given compound are readily determinable by those of skill in the art by a variety of means. A preferred means is to measure the physiological potency of a given compound that is a candidate for administration by the method of Davis et al. (1996), submitted to *Behavioral Neuroscience*. Briefly. excised patches and excitatory synaptic responses are measured in the presence of different concentrations of test compounds, and the differences in dosage response potency are recorded and compared. Davis, et al. found that one specific compound designated BDP-20 was about ten-fold more potent than another designated BDP-12 in a variety of behavioral (exploratory activity, speed of performance) and physical (excised patches and excitatory synaptic responses) tests. The relative physiological potency was an accurate measure of their behavioral potency. Thus, excised patches and excitatory synaptic responses may be used to gauge the relative physiological (and behavioral) potency of a given compound with regard to a known standard. (See also, Staubli, U. et al., 1994, *Proc. Nat. Acad. Sci.*, USE, 91:777–781 and Arai, A. et al., 1994, Brain Rcs., 638:343–346). A good correlation between physiological potency (increased AMPA currents) and behavioral effects has been observed. Thus, AMPA current modulation in vitro may be used to gauge the relative potency of a given compound for a biological response.

The dose of AMPA upmodulators needed to increase the level of neurotrophic factor or neurotrophic factor receptors to the desired degree can be determined by extrapolation from dose response studies in animals as described in Staubli et al., Proc. Natl. Acad. Sci. 91(23):11158–11162 (1994b), Staubli et al., Proc. Natl. Acad. Sci., 91(2):777–781 (1994a); and Grangeret: al., Synapse, 1S(4):326–329 (1993). Further, the desired dose of an AMPA upmodulator can be determined by assaying for an increase in neurotrophic factors or neurotrophic factor receptors.

Detecting Expression of Neurotrophic Factors or Receptors

Expression of neurotrophic factors or receptors thereof can be detected by any of a number of methods known to those of skill in the art. Thus, expression can be assayed using antibodies specific to neurotrophic factors or neurotrophic factor receptors as measured or determined by standard antibody-antigen or ligand-receptor assays, for example, competitive assays, saturation assays, or standard immunoassays such as ELISA or RIA. Various neurotrophic factors co-vary in expression. For example, expression of BDNF co-varies with the expression of NGF under a variety of conditions. Accordingly, determining changes in expression of one or more of these neurotrophic factors is generally informative with respect to other factors in this group.

Moreover, increases in the expression of a neurotrophic factor tends to co-vary with expression of its receptor. For example, TrkB levels co-vary with increases in BDNF. Thus, the changes in expression of either the neurotrophic factor or its receptor may be used to assess changes in the other. Monoclonal antibodies to neurotrophic factor receptors is well known in the art. See, for example, Eager, K., Onc. 6(5):819–824 (May 1991) and EP No. 91112109 (Pub. No. 0471205A1). Expression of neurotrophic factors or neurotrophic factor receptors can also be determined by assaying for the effects of these factors on target cells including the phosphorylation of receptor proteins and second messengers and the induction of immediate early genes such as c-fos.

In a further methods, expression of neurotrophic factors or neurotrophic factor receptors can be determined by assaying for their transcription (e.g., northern blots, in situ hybridization), or by identifying certain immediate-early gene products. These gene products can be evaluated for by RNA analysis or immunohistochemistry and are produced by certain genes which are activated about 30 minutes after receptor activation. See Collazo, et al., Neuron 9:643–656 (October 1992). For example, cells which have had their trk receptors activated will have demonstrable immediate-early gene products (such as Fos) in their nucleus.

Molecular biology assay methods are well known to those ot skill and may be found, for example, in Berger and Kimmel, Guide to Molecular Cloning Techniques Methods in Enzymology volume 152 Academic Press, Inc., San Diego, Calif. (Berger); Sambrook et al. (1989) Molecular Cloning—A Laboratory Manual (2nd ed.) Vol. 1–3; and Current Protocols in Molecular Biology F. M. Ausubel et al., eds., Current Protocols, a joint venture between Greene Publishing Associates, Inc. and John Wiley & Sons, Inc., (1994 Supplement) (Ausubel).

Kits

This invention provides for kits with unit doses of AMPA up-modulating drugs either in oral or injectable doses. In addition to the containers containing the unit doses will be an informational package insert describing the use and attendant benefits of the drugs in treating neurodegenerative pathologies not significantly affecting memory or learning. Preferred compounds and unit doses are those described herein above.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

EXPERIMENTAL

1. Demonstration of the increase in neurotrophic factor expression and neurotrophic factor receptor expression in an in vitro hippocampal preparation after treatment with an allosteric upmodulator.

Experiments employed the cultured hippocampal slice preparation because this preparation (1) provides mature neurons with relatively normal circuitry and association to glial cells (2) provides the possibility of directly applying drugs and assessing levels/types of neuronal activity. and (3) has previously been demonstrated to exhibit the "normal" patterns ot BDNF, NGF and TrkB mRNA expression (i.e., it appears the same as in vivo). Moreover, the slice preparation is advantageous because it is removed from other influences which might regulate BDNF expression in vivo (e.g., steroid hormones, inflammatory agents) (Saporito, M. S., et al., Mol. Pharm. 45: 395–401 (1994); Saporito, M. S., et al., Exp. Neurol. 123: 295–302 (1993)).

Organotypic hippocampal slice cultures were prepared from young rats (postnatal day 10–12) according to conventional methods (Rivera, S., et al., Mol. Brain Res. 27: 12–26 (1994); Stoppini, S., et al., J. Neurosci. Meth. 37: 173–182 (1991)). Specifically, 400 $\mu$m thick slices of hippocampus were explanted to thin, porous membranes and maintained in a bath of serum-based media in a humidified incubator (37° C., 5% $CO_2$). Following a 10 to 14 day maturation period, treatment with LiD37 (compound number 27 as shown in FIG. 1) was initiated by simply adding the drug to the incubation medium. LiD37 was added at concentrations of 0.05 uM, 10 uM, 20 uM, and 50 $\mu$M; control slices were left untreated or incubated in the presence of comparable additions of drug vehicle (0.01% DMSO). For treatment periods longer than 1 day, fresh media and LiD37 was added every 24 hrs. Slices were harvested (by fixation in paraforrnaldehyde) after treatment intervals of 1, 3, 10, 30, and 90 hrs. In separate experiments the receptor selectivity of the drug effect was tested by co-incubating the slices with AP5, an antagonist for the NMDA receptor, and CNQX an antagonist for the AMPA receptor.

In order to verify that effects of LiD37 were due to enhancement of normal synaptic activity, and not due to abnormal events such as drug-induced seizure activity, electrophysiological recordings were conducted on some slice cultures during acute and chronic exposure to LiD37. Field excitatory postsynaptic potentials (fEPSPs) were elicited along the Schaffer collateral pathway with bipolar twisted tungsten stimulation electrodes placed on either side of a glass micropipet recording electrode in stratum radiatum of hippocampal field CA1. By monitoring the shape and amplitude of dendritic fEPSPs evoked with alternate delivery of current pulses to the 2 stimulation electrodes, the effects of LiD37 synaptic activity were assessed. In one series of experiments, 50 μm LiD37 was infused for 30 min. after attainment of a stable baseline; in subsequent experiments evoked synaptic potentials and spontaneous activity were monitored at the conclusion of a 3 day treatment with 50 pm LiD37.

After fixation, the explants were cut into thinner sections; the tissue was mounted onto glass microscope slides and processed for in situ hybridization with $^{35}$S-cRNAs for BDNF or for its receptor TrkB for the localization and quantification of BDNF and TrkB mRNA levels (Gall, C., et al., In situ hybridization: A sensitive measure of activity dependent changes in neuronal gene expression., in In vitro/in vivo autoradiography and correlative imaging, W. E. Stumpf and H. F. Solomon, Editor; Academic Press: New York (1995)). In separate experiments In situ hybridization was used to measure mRNA levels for NGF. Hybridization densities were quantified by densitometric analysis of film autoradiograms using a computer based image analysis system with calibration relative to images of commercial radiolabeled standards exposed to each sheet of film.

The results indicated that treatment with LiD37 induced an increase in BDNF mRNA in the cultured hippocampal slice (Table I).

TABLE I

A. Time Course of Increases in BDNF mRNA Following LiD37 (50 μM) Treatment of Cultured Hippocampus.

| Time | Str. Granulosum | CA3 (SP)[1] | CA1 (SP) |
|---|---|---|---|
| 0 hr (con) | 0.51 ± 0.15[2] | 0.47 ± 0.06 | 0.04 ± 0.06 |
| 1 hr | 3.80 ± 2.18 | 1.19 ± 0.37 | 1.40 ± 0.63 |
| 3 hr | 3.29 ± 1.04" | 1.30 ± 0.32 | 1.32 ± 0.22 |
| 10 hr | 3.99 ± 0.54 | 2.99 ± 0.28 | 2.07 ± 0.50 |
| 30 hr | 2.70 ± 0.27' | 3.22 ± 1.18" | 2.49 ± 1.31* |

[1]SP = stratum pyramidale
[2]Units of measurements are uCi/g protein (mean +/− standard deviation). Statistical analysis: ANOVA with Tukey-Kramer post-hoc test for paired comparison. 'p < 0.05; "p < 0.01 versus paired vehicle-treated control (con).
B. Effect of LiD37 Dose on BDNF mRNA levels in the granule cell layer of Cultured Hippocampus (all 3 hr treatments)

| Dose | Str. Granulosum |
|---|---|
| 0 (vehicle) | 0.350 ± 0.21 |
| 10 uM | 0.908 ± 0.28' |
| 20 uM | 1.532 ± 0.83* |
| 50 uM | 1.58 ± 0.53" |

Values are densitometric measures of BDNF cRNA labeling (mean±std. dev.; uCi/g) Significance was assessed using the one way ANOVA (P=0.0019 for main effect of treatment) followed by the Student-Newman-Kuels test for paired comparisons ('P<0.05, "P<0.01, *P<0.001).

Labeling was increased in both the granule cell and pyramidal cell neuronal layers and was not increased in the intervening molecular layers. This represents an increase in BDNF mRNA in cells that normally make this neurotrophin, and demonstrates that the drug did not induce aberrant expression in glial cells and interneurons (outside the major cell layers) that do not normally make this factor. Quantification of hybridization densities in tissue from the experiment demonstrated somewhat different temporal parameters in the granule cells and in the pyramidal cells of regions CA3 and CA1 (Table I). Hybridization was rapidly increased in the granule cells but increased more slowly (through 30 hrs) in the pyramidal cells. In separate experiments, the increase in BDNF mRNA was not blocked by the addition of AP5 but was blocked by the addition of 20 uM CNQX, to the incubation medium. This is consistent with results of previous studies indicating that activity-induced increases in BDNF expression by hippocampal neurons can be mediated independently by the AMPA class of glutamate receptor (Zafra, F., et al., EMBO J 9: 3545–3550 (1990)).

Separate experiments demonstrated (1) no increase in BDNF mRNA with LiD37 doses of 0.5 uM, (2) progressively larger increases in BDNF mRNA at 10, 20, and 50 uM. (Table IB), (3) increased TrkB mRNA (2.5 fold over the control value) in the granule cells with 24hr treatment with LiD37 at 50 μM (Table II): (4) increased BDNF mRNA in both the granule cells and pyramidal cells following treatment with the positive AMPA modulatory drugs DP75 (50 uM), GR120 (200 uM) and GR87 (Table II)

TABLE II

In situ hybridization measures of BDNF and TrkB mRNA levels in hippocampus following treatment with AMPA receptor modulators. Calibrated densitometric measures of $^{35}$S-cRNA labeling.

A) BDNF mRNA[3]

| Treatment | Str. Granulosum | Str. Pyramidale (CA1) |
|---|---|---|
| Control (vehicle) | 0.715 ± 0.26[22] | 0.935 ± 0.233 |
| DP75[1] (3 hr) | 3.95 ± 0.90* | 3.26 ± 0.78* |

B) Trk B mRNA

| Treatment | Str. Granulsom |
|---|---|
| control (vehicle) | 1.05 ± 0.13 |
| LiD37 (24 hr) | 2.44 ± 0.18" |

C) NGF mRNA

| Treatment | Str. Granulosm |
|---|---|
| Control (vehicle)-3 hr | 0.157 ± 0.04 |
| LiD37-3 hr | 0.662 ± 0.12* |
| LiD37-24 hr | 0.085 ± 0.031 |

[1]Both DP75 and LiD37 were applied at 50 uM.
[2]Values are densitometric measures of BDNF, TrkB, and NGF cRNA labeling (mean ± std. dev.; uCi/g). Significance was assessed using the one tail Student's T test for A and B, and by the one way ANOVA followed by the Student's-Newman-Kuels post hoc text for C ("P < 0.01, *P < 0.001). For C, the main effect of treatment, P < 0.0001; considered extremely significant.
[3]BDNF mRNA levels were also significantly increased by 3 hr treatment with the AMPA modulators GR87 (200 uM; P = 0.033 for stratum granulosum), and GR120 (250 uM; P = 0.005 for both CA1 and stratum granulosum).

Electrophysiological recording from treated slices demonstrated that 30 min. infusion with 50 μM LiD37 was sufficient to increase evoked potential amplitude (consistent with amplification of AMPA currents) without evidence of pathophysiology. Recordings from slices treated chronically at this dose (3 days) also exhibited healthy, normal appearing evoked potentials and no evidence for seizures.

The AMPA modulator also altered BDNF mRNA in vivo. Alert, adult Sprague Dawley rats were given a single intraperitoneal injection of (i) the AMPA modulatory ("ampakine") drug GR120 at a dose of 6 mg/kg (n=4) or (ii) vehicle (n=4) and placed individually in an open Field for 1.5 hrs. After this period. the rats were killed by an overdose of sodium pentobarbital, intracardially perfused with 4% paraformaldehyde. and their brains sectioned and processed for in situ hybridization of BDNF $^{35}$S-cRNA. In situ hybridization labeling was measured to assess BDNF mRNA levels in several brain areas including the parietal neocortex, piriform cortex and claustrum. The drug GR120 induced a mean 50% increase in the ratio of claustrum to piriform cortex BDNF mRNA levels (i.e., claustrum/piriform cortex measures; p<0.002, Student's t test).

2. Demonstration of an in vitro method to assess the allosteric upmodulating effects of compounds using hippocampal explants.

The physiological effects of AMPA upmodulating- compounds can be tested in vitro with slices of rat hippocampus according to the following procedure. Excitatory responses (field EPSPS) are measured in hippocampal slices, which are maintained in a recording chamber continuously perfused with artificial cerebrospinal fluid (ACSF). During a 15–30 minute interval. the perfusion medium is switched to one containing various concentrations of the test compounds. Responses collected immediately before and at the end of drug perfusion are superimposed in order to calculate both the percent increase in EPSP amplitude and percent increase in the width of the response at one-half the peak height (half-width).

To conduct these tests, the hippocampus is removed from anesthetized, 2 month old Sprague-Dawley rats and in vitro slices (400 micrometers thick) are prepared and maintained in an interface chamber at 35° C. using conventional techniques (see, for example, Dunwiddie and Lynch. J. Physiol. 276:353–367 (1978)). The chamber is constantly perfused at 0.5 ml/min with ACSF containing (in mM): NaCl 124, KCl 3, $KH_2PO_4$ 1.25, $MgSO_4$ 2.5, $CaCl_2$ 3.4, $NaHCO_3$ 26, glucose 10 and L-ascorbate 2. A bipolar nichrome stimulating electrode is positioned in the dendritic layer (stratum radiatum) of the hippocampal subfield CA1 close to the border of subfield CA3. Current pulses (0.1 msec) through the stimulating electrode activate a population or the Schaffer-commissural (SC) fibers which arise from neurons in the subdivision CA3 and terminate in synapses on the dendrites of CA1 neurons. Activation of these synapses causes them to release the transmitter glutamate. Glutamate binds to the post-synaptic AMPA receptors which then transiently open an associated ion channel and permit a sodium current to enter the postsynaptic cell. This current results in a voltage in the extracellular space (the field excitatory post-synaptic potential or field "EPSP") which is recorded by a high impedance recording electrode positioned in the middle of the stratum radiatum of CA1.

For experiments to judge the potency of a compound AMPA derived currents, the intensity of the stimulation current is adjusted to produce half-maximal EPSPs (typically bout 1.5–2.0 mV). Paired stimulation pulses are given every 40 sec with an interpulse interval of 200 msec (see below). The field EPSPs of the second response are digitized and analyzed to determine amplitude, half-width, and response area. If the responses are stable for 15–30 minutes (baseline), test compounds are added to the perfusion lines for a period of about 15 minutes. The perfusion is then changed back to regular ACSF.

Paired-pulse stimulation is used since stimulation the SC fibers, in part, activates intemeurons which generate an inhibitory postsynaptic potential (IPSP) in the pyramidal cells of CA1. This feed forward IPSP typically sets in after the EPSP reaches its peak. It accelerates the repolarization and shortens the decay phase of the EPSP, and thus could partially mask the effects of the test compounds. One of the relevant features of the feed-forward IPSP is that it can not be reactivated for several hundred milliseconds following a stimulation pulse. This phenomenon can be employed to advantage to eliminate IPSP by delivering paired pulses separated by 200 milliseconds and using the second ("Primed") response for data analysis.

The field EPSP recorded in field CA1 after stimulation of CA3 axons is known to be mediated by AMPA receptors: the receptors are present in the synapses (Kessler et al., Brain Res. 560:337–341 (1991)) and drugs that selectively block the receptor selectively block the field EPSP (Muller et al., Science 242:1694–1697 (1988)). Aniracetam increases the mean open time of the AMPA receptor channel and thereby increases the amplitude of the synaptic current and prolongs its duration (Tang et al. Science 254:288–290 (1991)). These effects are mirrored in the field EPSP, as reported in the literature (see, for example, Staubli et al., Psychobiology 18:377–381 (1990); Xiao et al., Hippocampus supra; Staubli et al., Hippocampus 2:49–58 (1992)). Similar results have been reported for the previously disclosed stable benzamide derivatives of aniracetam, where increases in the amplitude of the field EPSP of 60% were observed (International Patent Application Publication No. WO 94/02475 (PCT/US93/06916) (Lynch and Rogers, Regents of the University of California)). A subset of AMPA-receptor modulators increases the half-width of the EPSP response by several hundred percent. This feature is useful in predicting physiological effects.

All publications and patents mentioned in this specification are herein incorporated by reference into the specification to the same extent as if each individual publication or patent was specifically and individually indicated to be incorporated herein by reference.

What is claimed is:

1. A method for increasing the level of neurotrophic factors in a brain of a mammal afflicted with a pathology which produces neurodegeneration without significant loss of memory or learning, said method comprising:

administering to said mammal an amount of AMPA-receptor allosteric upmodulator effective to increase the expression of neurotrophic factors in said brain of said mammal.

2. The method according to claim 1, wherein said pathology is selected from the group comprising: Parkinson's Disease, amyotrophic lateral sclerosis (ALS), stroke, direct trauma, Huntington's disease, epilepsy, Down's Syndrome, hypoglycemia, and hypoxia.

3. The method according to claim 2, wherein said pathology is selected from the group comprising: Parkinson's disease, ALS, Huntington's disease, hypoglycemia, and Down's syndrome.

4. The method according to claim 1, wherein said mammal is a human.

5. The method according to claim 1, wherein said neurotrophic factors are selected from the group consisting of: brain derived neurotrophic factor, fibroblast growth factors, neurotrophin 3, nerve growth factor, neurotrophin 4/5, glial cell line derived neurotrophic factor, ciliary neurotrophic factor, leukemia inhibitory factor, transforming growth factors, and platelet-derived growth factor.

6. The method according to claim 5, wherein said neurotrophic factors are selected from the group consisting of: brain derived neurotrophic factor, glial cell line derived neurotrophic factor, and ciliary neurotrophic factor.

7. The method according to claim 6, wherein the neurotrophic factor is brain derived neurotrophic factor.

8. A method for increasing the level of neurotrophic factor receptors in a brain of a mammal in need of increased neurotrophic factor receptors, wherein the mammal is afflicted with a pathology which produces neurodegeneration without significant loss of memory or learning, said method comprising:

administering to said mammal an amount of allosteric upmodulator of AMPA receptors effective to increase the expression of said neurotrophic factor receptors.

9. The method according to claim 8, wherein said allosteric modulator is LiD37 or D1.

10. The method according to claim 8, wherein the allosteric upmodulators are blood-brain barrier permeant.

11. The method according to claim 8, wherein the neurotrophic receptor is the TrkB receptor.

12. A method for increasing the level of neurotrophic factors in the nervous tissue of a mammal, said method comprising:

administering to said mammal an amount of AMPA-receptor allosteric upmodulator effective to increase the expression of neurotrophic factors in said nervous tissue.

13. A method according to claim 12, wherein said nervous tissue is nervous tissue on the brain side of the blood brain barrier.

* * * * *